United States Patent [19]

Chronister

[11] Patent Number: 5,106,304
[45] Date of Patent: Apr. 21, 1992

[54] DENTAL RESTORATION COMPOSITION AND METHOD

[76] Inventor: Stephen H. Chronister, 1005 South Topeka Blvd., Topeka, Kans. 66612

[21] Appl. No.: 594,861

[22] Filed: Oct. 9, 1990

[51] Int. Cl.$^5$ ............................................. A61C 5/00
[52] U.S. Cl. ................................... 433/228.1; 106/35
[58] Field of Search ............... 433/228.1, 212.1, 201.1, 433/173, 174, 175, 215; 106/35; 523/116

[56] References Cited

U.S. PATENT DOCUMENTS

| | | | |
|---|---|---|---|
| 2,508,816 | 5/1950 | DeMent | 524/560 |
| 2,549,180 | 4/1951 | DeMent | 106/35 |
| 4,810,195 | 3/1989 | Asmussen et al. | 433/226 |

Primary Examiner—Cary E. O'Connor
Attorney, Agent, or Firm—Litman, McMahon & Brown

[57] ABSTRACT

A dental filling and sealing composition and method for human tooth restoration. The method includes pulverizing bovine teeth into small particles and separating the particles containing only enamel from the remaining particles and mixing with an adhesive such as gloss ionomer cement, methyacrylate or the like. For restoration using a glass ionomer cement, the enamel particles are mixed directly with the cement and applied to a human tooth by techniques commonly known in the dental profession. For restoration using an acrylic adhesive, the enamel particles are subjected to an acid-etch treatment followed by forming a mixture comprising the enamel particles and the acrylic adhesive, which is applied by commonly known techniques.

6 Claims, No Drawings

DENTAL RESTORATION COMPOSITION AND METHOD

BACKGROUND OF THE INVENTION

The present invention relates to a material and method for filling and otherwise restoring human teeth.

Historically, dentists have utilized various metals and metal amalgamations to fill cavities and otherwise replace missing or removed tooth structure. However, tooth restoration with such metals does have certain deficiencies, one of the principal deficiencies being the aesthetic appearance of the metal.

Numerous organic compounds have also been used in a variety of mixtures and proportions in an attempt to discover materials for dental composites and restoratives that would have improved characteristics as compared to the metals. Dental composite and restorative materials must not only have good forming characteristics in order to be shaped to fit a cavity or be molded in place to repair chipped or damaged teeth but must also have physical and chemical properties which are compatible with a dental, physiological environment, such as thermal coefficient of expansion, non-toxic, insoluble, non-corrosive, etc.

Further, such restorative compositions must exhibit satisfactory hardness and durability characteristics in order to meet the requirements of their intended purpose. In attempts to satisfy the hardness and durability characteristics, researchers have utilized various compounds often including some type of resin integrated with various amounts of particulate material, such as organic polymers, various kinds of metals, ceramics, and the like. Such compounds usually also include other materials, such as pigments, catalysts, handling agents and opacifiers, and the like, for aesthetic and other purposes.

When such restorative materials are placed in the mouth, the materials must securely bond both to itself integrally and to a tooth being restored. Since the final bonding occurs during installation in the mouth, it is particularly essential that satisfactory adhesion be obtainable in the environment of the mouth.

One method which has been utilized to enhance securement of composites and adhesives to tooth enamel is to severely etch the enamel with a highly acidic solution. This procedure intentionally demineralizes the enamel and creates deep pits and irregularities in the surface of the enamel to provide mechanical interlocking with the underlying tooth structure as the primary means of retention of the restorative. Although such etching of the underlying tooth structure for bonding purposes usually does provide adequate adhesion, it also causes deteriorative effects on the underlying tooth structure.

Another method which has helped alleviate such destructive treatment of the underlying tooth structure is the utilization of an adhesive, such as a glass ionomer cement which bonds strongly and directly to the tooth structure. Glass ionomer cements consist of a particulate glass powder and a mixing fluid which may generally be described as an aqueous solution of a polycarboxylic acid. The diameter range of particles in the glass powder must be suitable for dental applications. The particle size and size distribution of the glass particles can be adjusted using conventional techniques, such as by grinding, screening, sedimentation or other particle classification methods. Control of the range and distribution of particle size is an important characteristic for influencing the strength, work time and set time of the cement.

Work time and set time can also be adjusted by affecting the surface area of the glass particles, such as by etching with an acid and thoroughly washing the treated glass to leave substantially no soluble calcium salts on the surface of the glass particles.

One process for making glass ionomer cement powder involves comminuting carboxylic acid with a chemically active glass, such as an aluminosilicate glass which has been prepared with a fluoride flux. The work time and set time of the cement may be influenced by the molecular weight and carboxyl equivalent weight of a particular polyacid or by the relative quantity of carboxylic acid added during the comminution step. For example, a low relative quantity of carboxylic acid, such as approximately 3% by weight or less, will extend work time without substantially affecting set time. Such characteristics are generally desired for luting cements, veneer cements or orthodontic bracket adhesives. Similarly, a larger relative quantity of carboxylic acid, such as approximately 5% by weight or more, will extend both work time and set time. Such characteristics are generally desired for endodontic sealants or bone cements and for applications where high glass loading levels are desired, such as for basing cements, crown build-up cements or posterior liners.

In addition to controlling particle size distribution and area of the glass, selection of a polyacid, and adjusting the ratio of glass to polyacid, work time and set time of the cement may be further adjusted by the addition of a chelating agent, such as tartaric acid or the like.

To form the glass ionomer cement, the glass particles and acid are comminuted under sufficiently vigorous, substantially anhydrous pulverization conditions, such as by ball milling, to cause reaction between the glass and carboxylic acid such that carboxylate salt is formed in the glass powder. The comminution must be conducted under substantially anhydrous conditions as the presence of moisture can result in the formation of carboxylate salt having entrained water, which results in poor mix properties and shortened work times. The comminuted glass and carboxylic acid forms a water-hardenable cement.

When actually using the glass ionomer cements to restore a tooth, a solvent, such as water, is added to the cement, whereupon multivalent ions, such as calcium ions, leach from the glass and cross-link the carboxylic acid chains during curing which results in formation of the restorative composition. The mixture undergoes a brief working period, during which the reactants are converted from a creamy paste to a relatively firm, carvable solid. The working period is followed by a brief setting period, during which the carvable solid becomes sufficiently strong to function as a dental cement.

Glass ionomer cements have generally enjoyed widespread application since they generally exhibit excellent adhesion characteristics to calcified tooth structure, including both enamel and dentin tooth substances. Besides superior adhesion characteristics, glass ionomer cements also excel in marginal sealing and durability in the mouth over a long period of time. In addition, glass ionomer cements generally exhibit little or no irritant action, detrimental corrosion, or other harmful pathological action upon the dental pulp. Further, glass ionomer cements maintain excellent resistance to the mouth tissues or fluids over extended periods of time.

Unfortunately, however, glass ionomers have not been particularly useful for certain applications. For example, glass ionomers by themselves are visually inferior to composite resins. As a restorative, glass ionomers are extremely sensitive to technique and usually are not polishable. Glass ionomer cements are usually overly brittle which limits their use in the molar region and at corners and edges of a tooth.

Further, a glass ionomer generally has a relatively weak cohesive strength. As a result, the glass ionomer bonds more strongly to the underlying tooth structure than it bonds to itself. This is sometimes observed where a filling comprising a glass ionomer fails; the failure occurs within the bulk of the glass ionomer while the bond between the tooth and the glass ionomer remains intact.

To compensate for some of the deficiencies of glass ionomer cements, the cement powder can contain or be combined with appropriate quantities of viscosity modifiers such as microfine silica, wetting agents, milling agents, extending fillers, radiopacifiers, metal powders such as silver or silver alloys, medicants, and the like. In addition, such a composition may include materials having beneficial aesthetic properties such as adjuvants including pigments for matching those of natural healthy human teeth, plaque repellency, polishability and opacity.

Another approach used to prepare a composition for restoring teeth involves imbedding glass particles in a binder, such as methyacrylate which usually achieves good bonding characteristics with the underlying tooth structure. Unfortunately, the methyacrylate does not simultaneously achieve acceptable bonding with the glass particles imbedded therein unless they have been subjected to acid etching.

A suitable, self-adhering dental restorative should preferably provide certain beneficial attributes at the juncture between the restorative and the abutting tooth structure or at the exposed surfaces thereof. Such attributes include availability of leachable calcium, availability of leachable fluoride to minimize the formation of secondary caries, sealing characteristics to minimize microleakage by providing a substantially impervious protective barrier, hydrophilic characteristics sufficient to adequately wet dentine in vivo, an ability to bond to both dentin and enamel, natural appearance, optimal placement consistency, substantially pH-neutrality for maximum healing potential, extremely low solubility and disintegrability, and non-bioresorbability. One of the principal benefits of glass ionomer cement or methacrylate lies in the fact that such materials for tooth restoratives can be placed directly on or into a human tooth without any underfilling or other similar measures and obtain a result which is physiologically satisfactory cosmetically and mechanically and substantially meet the above noted criteria.

The major drawback in using glass ionomer cement or methacrylate in tooth restoration is that such compositions tend to wear relatively quickly when used in locations where teeth engage or where wear otherwise frequently occurs.

There is a definite need for a dental filling and sealing composition which requires minimal removal of healthy tooth structure while providing a strong, permanent, long-wearing restoration having a pleasing, natural appearance. Such a composition should possess good bonding internally as well as with the underlying tooth structure and should possess structural properties which closely match those of natural healthy teeth, such as cohesive strength, wearability, coefficient of thermal expansion and durability.

SUMMARY OF THE INVENTION

An improved composition and method are provided for filling dental cavities and for other dental restoration having a substantially natural enamel appearance and being relatively long-wearing. A filler comprising finely ground particles is prepared from enamel of animal teeth. The animal teeth are first sterilized and pulverized. The unwanted portions of the animal teeth are then separated from the particles containing only enamel. The enamel particles are then separated into ranges of particle sizes, with the particular range of sizes depending on the particular application, with an example range being approximately 10–100 microns. The bonding and wearing characteristics of the enamel particles when embedded in a bonding matrix for restoring human teeth are enhanced by subjecting the particles to various acid and alkaline baths in order to etch and desiccate the enamel particles. Preferably the animal teeth are bovine teeth.

The filler comprising the selected range of ground or comminuted tooth enamel is mixed with binding means suitable for fixedly binding to enamel of a tooth to be repaired by the composition and being non-injurious or non-harmful when used on the tooth of a human. Suitable binding means include methyacrylate and preferably is a glass ionomer cement.

Combining the enamel particles with the translucency of the glass ionomer cement or the methyacrylate provides naturally appearing fillings and restoratives, which are pleasing and naturally appearing aesthetically and which bond directly to the tooth, substantially eliminating the destructive treatment of the underlying tooth structure observed with other dental techniques. Also, by intermingling the enamel particles in the bulk of a filling and binding material, such as the glass ionomer cement or the methyacrylate, wherein the strength of the bond between the binding material and the enamel particles is greater than the strength of the bond of the binding material to itself, internal cross-linking occurs between the binding material and the enamel particles which enhances the cohesive strength of the mixture.

For those applications where it is desired to use an ionomer cement, the animal enamel particles are intimately mixed with the glass ionomer cement and applied in accordance with techniques commonly known in the dental profession. For those applications where it is desired to use an acrylic, such as methyacrylate, the animal enamel particles are acid etched to achieve desired micromechanical, internal bonding and are then appropriately mixed with the acrylic and applied in accordance with commonly known techniques.

OBJECTS OF THE INVENTION

Therefore, the objects of the present invention are: to provide a strong, durable, polishable material for dental restoratives; to provide such a material that is relatively long-wearing; to provide such a material with a substantially natural enamel coloring with improved color stability; to provide such a material with a more naturally appearing hue; to provide such a material which forms strong and reliable bonds both internally and with the underlying enamel and dentin structure of a human tooth; to provide such a material having internal cross-linking such that cohesive strength of the material is enhanced; to provide such a material which minimizes or eliminates the need for undercutting in order to retain fillings and other restorations made therefrom; to provide such a material which has a translucency closely approximating that of a normal human tooth; to provide such a material which exhibits corrosion resistance in a human oral environment; to provide such a material which is adaptable for mounting in a moist oral environment; to provide such a material which can be used for inlays, onlays, crowns, bridgework or orthodontic appliances and other dental applications; to provide such a material which has desirable working and setting times; to provide a method of tooth restoration using such a material; and to generally provide such a material which is relatively easy and inexpensive to manufacture and which generally performs the requirements of its intended purposes.

Other objects and advantages of this invention will become apparent from the following description wherein are set forth, by way of illustration and example, certain embodiments of this invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

In an application of the present invention, tooth restoration shall mean facing, filling, replacing, rebuilding, or the like, of a tooth or missing portions thereof caused by decay, breakage, or the like. For discussion purposes and without limiting the application of the present invention, examples are provided herein to demonstrate one or more of the many uses available for applications of the invention.

The present invention generally includes imbedding a matrix of ground or pulverized filling material in a binding or adhesive means. The adhesive means is preferably tightly and strongly bonding to tooth enamel and is compatible for use in the human mouth with respect to safety and organoleptic properties such as taste. Adhesive means include glass ionomer cement, methyacrylate, or the like. The pulverized filling material comprises tooth enamel which, for purposes of the present invention, may be obtained from animal teeth, including tusks, preferably of bovine origin. Bovine teeth not only provide the desired characteristics but are readily available and plentiful.

The imbedding of pulverized animal tooth enamel provides substantially greater surface area of tooth enamel which generally forms a stronger bond with the adhesive means than the adhesive means forms with itself. As a result, cross-linking occurs between the adhesive means and the pulverized animal tooth enamel such that the cohesive strength of the restorative is substantially greater than is obtainable from the adhesive means alone. Also, the animal tooth enamel provides substantially greater wearability characteristics than is generally obtainable with adhesive means without such imbedded animal tooth enamel. Such an arrangement also enhances the abrasion resistance of the restorative.

The binder material preferably allows the pulverized tooth enamel contained therein to color the composite composition such that a natural tooth enamel color is presented by the composition in use. It is foreseen that pulverized tooth enamel of various colors may be selected to better match the color of the teeth being restored or, if the color cannot be closely matched with the pulverized tooth enamel, additional pigments of the type currently used may be incorporated in the composition.

Animal teeth to be used for preparation of the pulverized filling material are obtained from any appropriate source, such as from a meat packing plant. Before processing such teeth, they are subjected to a sterilization procedure and may be sorted as to color. In one application of the present invention, the teeth are sterilized by boiling in water for approximately eight hours. This procedure also coagulates proteins in the teeth. Following sterilization, the animal teeth are desiccated, such as by placement at an elevated temperature in a drying oven.

After sterilization, the animal teeth are crushed into coarse particles to expose dentin and non-enamel material contained in the teeth. In one application of the present invention, the teeth are crushed in a hammermill, with the resulting particles ranging from approximately 1 to 5 millimeters in size.

After exposing the dentin and non-enamel material, it is then essential to separate the enamel therefrom. As an example, the teeth particles are boiled in a solution of concentrated sodium hydroxide for approximately 16–20 hours in order to hydrolyze the organic bond between the enamel and the dentin in the teeth particles. After boiling, the teeth particles are subsequently allowed to cool, rinsed with water, pH-neutralized with an inorganic acid, and desiccated with acetone.

The tooth enamel particles are then further finely crushed or pulverized, such as in a hammermill. In one application of the present invention, the enamel particles are finely crushed into particles ranging from approximately 10 to 200 microns in size.

After cleaning and desiccating with acetone, the fine enamel particles are separated from the fine dentin and non-enamel particles. In one application of the present invention, the fine enamel and dentin particles are separated by placing the finely crushed particles in a concentrated, saturated solution of zinc iodide. Since the zinc iodide solution has a specific gravity which lies between the specific gravity of the fine enamel particles and the specific gravity of the fine dentin particles, the fine enamel particles sink to the bottom of the container containing the zinc iodide while the fine dentin particles rise to the top of the zinc iodide solution. It is then a simple matter to pour off the zinc iodide solution along with the floating fine dentin particles, leaving the fine enamel particles in the container. The fine enamel particles are then washed with water and dried with acetone.

The fine enamel particles are then separated into narrower ranges of particle sizes, with each particular range of particle sizes depending on the type of restoration work to be performed therewith. For example, laboratory sieves may be used to select fine enamel particles ranging from approximately 1 to 100 microns in size for a particular restoration.

As an example of preparing material for a tooth restorative using the fine enamel particles with a glass ionomer cement, a mixture is formed by admixing the components and stirring that contains approximately 85% by weight of a glass ionomer cement in the form of a powder, such as that disclosed in U.S. Pat. No. 4,342,677, which is incorporated herein by reference, and approximately 15% or more by weight of fine enamel particles ranging from 1–100 microns in size as hereinbefore described. The combined mixture of glass ionomer cement and enamel particles is then mixed with carboxylic acid solution in an approximate ratio of 4.5 grams of mixture to 1 gram of acid solution, with the resulting material then applied as a restorative by techniques commonly known and applied in the dental profession.

For those applications where it is desired to use a composite comprising a matrix of an acrylic material filled with the fine enamel particles, further processing of the enamel particles is preferred as follows. The fine enamel particles are chemically etched to promote micro-mechanical bonding between the acrylic component and the fine enamel particles. In one application of the present invention, the fine enamel particles are treated with a 30% by weight phosphoric acid solution for approximately 60 seconds, followed by rinsing with water and then treating with a 1% by weight sodium fluoride solution for approximately 8 hours. The neutralized particles are then thoroughly rinsed with water and dried with acetone.

As an example of preparing material for a tooth restorative using such fine enamel particles in an acrylic matrix, the fine enamel particles are kneaded into an acrylic component such as that disclosed in U.S. Pat. Nos. 4,503,169 and 4,719,149 which are incorporated herein by reference. The resulting material is then applied as a restorative by techniques commonly known and applied in the dental profession.

Broadly speaking, an application of the present invention first involves preparation of the tooth to be restored, such as by first removing the decayed portion of the tooth and leaving underlying dentin and enamel surfaces exposed. Such initial decay removal can be performed by any appropriate technique, such as by the use of caries removal materials which may be advantageous for the reduction of patient discomfort, or by conventional drilling, or the like.

The exposed tooth structure is then preferably cleaned of all debris and dried. This is particularly important since surfaces in the oral environment are usually coated with water and organic matter, such as proteins, bacteria, and food residue which are deposited on the surfaces by saliva. Washing the exposed tooth structure with a dilute acid solution will generally remove the undesired organic matter, leaving the surface more suitable for bonding. The exposed structure is then rinsed clean of the acid wash and dried, such as with clean, dry compressed air or with a solvent, such as acetone, which carries away water as an azetrope.

While bovine teeth have been described herein as a source of enamel for use in the invention, it is foreseen that enamel of other animals, including humans, could be utilized. Likewise, it is foreseen that other adhesive agents besides those specifically described could be utilized in the invention provided such adhesive agents bond well to enamel and are not otherwise unacceptable because, for example, the agent is poisonous to humans, does not have acceptable wear even when combined with a hard material such as the enamel, requires too much time to harden after use or has a lingering taste.

It is to be understood that while certain forms of the present invention have been illustrated and described herein, it is not to be limited to the specific forms or arrangement of parts described and shown.

What is claimed and desired to be secured by Letters Patent is as follows:

1. A method for preparing enamel for restoring a human tooth, comprising the steps of:
    (a) obtaining bovine teeth;
    (b) sterilizing and coagulating proteins in said bovine teeth by boiling in water sufficiently to kill living organisms in said bovine teeth;
    (c) desiccating said bovine teeth at an elevated ambient temperature;
    (d) crushing said bovine teeth into coarse particles;
    (e) hydrolyzing organic bonding between enamel and dentin of said coarse particles by boiling in concentrated sodium hydroxide;
    (f) cooling and rinsing said coarse particles with water;
    (g) neutralizing the pH of said coarse particles;
    (h) desiccating said coarse particles;
    (i) further crushing said coarse particles into fine particles having dimensions of less than about 200 microns such that a first portion of said fine particles comprises substantially enamel material and a second portion of said fine particles comprises substantially dentin material;
    (j) cleaning and desiccating said fine particles;
    (k) separating said first portion from said second portion by placing said fine particles in a solution having a density intermediate said first and second portions;
    (l) pouring off said solution with said second portion suspended therein;
    (m) washing said first portion with water; and
    (n) drying said first portion.

2. The method according to claim 1 including the subsequent steps of:
    (a) forming a mixture comprising said first portion having a selected range of particle sizes and adhesive means; and
    (b) restoring a tooth by applying said mixture to a tooth structure prepared for such restoration.

3. The method of claim 2 wherein step (a) includes:
    (a) preparing a mixture of glass ionomer powder and said first portion having enamel particles ranging in size from 1 to 100 microns such that said glass ionomer powder comprises approximately 85% of said mixture and said first portion comprises the remainder of said mixture; and
    (b) preparing material for a restorative by mixing said mixture with a carboxylic acid solution in an approximate ratio of 4.5 grams of said mixture to 1 gram of said solution.

4. The method according to claim 1, including the subsequent steps of:
    (a) submerging said first portion into a phosphoric acid solution;
    (b) rinsing said first portion with water;
    (c) submerging said first portion in a sodium fluoride solution;
    (d) rinsing said first portion with water;
    (e) desiccating said first portion;

(f) forming a mixture comprising said first portion having a selected range of particle sizes and adhesive means; and
(g) restoring a tooth by applying said mixture to a tooth structure prepared for such restoration.

5. The method of claim 4 wherein:
(a) said adhesive means is methyacrylate.

6. A method for preparing enamel for restoring a human tooth, comprising the steps of:
(a) submerging bovine teeth in boiling water;
(b) crushing said bovine teeth into coarse particles;
(c) hydrolyzing organic bonding between enamel and dentin of said coarse particles by boiling in concentrated sodium hydroxide;
(d) neutralizing the pH of said coarse particles;
(e) crushing said coarse particles into fine particles such that a first portion of said fine particles comprises substantially enamel material and a second portion of said fine particles comprises substantially dentin material; and
(f) separating said first portion from said second portion.

* * * * *